United States Patent [19]

Thelen

[11] Patent Number: 4,960,959

[45] Date of Patent: Oct. 2, 1990

[54] PROCESS FOR THE MANUFACTURE OF ALKYNEDIOLS BY REACTION OF KETONES WITH ACETYLENE

[75] Inventor: Gerhard Thelen, Nottuln, Fed. Rep. of Germany

[73] Assignee: Huels Aktiengesellschaft, Marl, Fed. Rep. of Germany

[21] Appl. No.: 381,996

[22] Filed: Jul. 17, 1989

Related U.S. Application Data

[63] Continuation of Ser. No. 176,232, Mar. 31, 1988, abandoned.

[30] Foreign Application Priority Data

Apr. 4, 1987 [DE]  Fed. Rep. of Germany ....... 3711382

[51] Int. Cl.$^5$ .................... C07C 29/42; C07C 33/042; C07C 33/14; C07C 33/26
[52] U.S. Cl. .................... 568/855; 568/807; 568/816; 568/856; 568/874
[58] Field of Search ............... 568/855, 856, 874, 807, 568/816

[56] References Cited

U.S. PATENT DOCUMENTS

| | | | |
|---|---|---|---|
| 2,163,720 | 6/1939 | Vaughn | 260/617 |
| 2,385,546 | 9/1945 | Smith et al. | 260/658 |
| 2,385,548 | 9/1945 | Smith et al. | 260/658 |
| 2,445,058 | 7/1948 | Fields | 130/77 |
| 2,979,535 | 4/1961 | Sennewald et al. | 568/855 |
| 3,462,499 | 8/1969 | Tedeschi et al. | 568/855 |
| 4,117,249 | 9/1978 | De Simone et al. | 260/635 Y |

FOREIGN PATENT DOCUMENTS

1329815 9/1973 United Kingdom .
1354011 5/1974 United Kingdom .

OTHER PUBLICATIONS

Weast, Robert, Handbook of Chemistry and Physics, Chemical Rubber Co., Cleveland, Ohio 1970-1971, 51st ed., p. C-293.

Jacobs et al., Chemical Analysis of Industrial Solvents, Interscience Publishers Inc., New York, New York, 1953, p. 43.

Einfuhrung der Athinyl-und Aklinyl-Gruppe in Organische Verbindungen, Dr. Willi Ziegenbein, Chemische Werke Huls, pp. 48-115.

*Primary Examiner*—J.E. Evans
*Attorney, Agent, or Firm*—Oblon, Spivak, McClelland, Maier, & Neustadt

[57] ABSTRACT

A process for manufacturing an alkynediol is disclosed. In this process, a $C_{3-12}$ ketone is reacted with acetylene in the presence of potassium hydroxide in an $C_{1-4}$ alkyl-tert-butyl ether solvent. The potassium hydroxide is used in a molar ratio, relative to the amount of ketone used, of from 1.0:1.0 to 1.6:1.0.

9 Claims, No Drawings

PROCESS FOR THE MANUFACTURE OF ALKYNEDIOLS BY REACTION OF KETONES WITH ACETYLENE

This application is a Continuation of application Ser. No. 07/176,232, filed on Mar. 31, 1988, now abandoned.

BACKGROUND OF THE INVENTION

1. Field of the Invention:

This invention relates to the manufacture of alkynediols.

2. Discussion of the Background:

A series of manufacturing procedures have been described for the manufacture of alkynediols of the general formula I

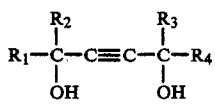

In the case of aldehydes, formaldehyde and acetaldehyde can be readily converted with acetylene to the corresponding monoalcohols and glycols using Reppe's ethinylation process which use a copper acetylide catalyst. That method yields unsatisfactory results however if higher aldehydes are used.

Particular difficulties are experienced with the reaction of two moles of a ketone with one mole of acetylene. For that reaction to proceed at least one mole of a base is required. Previously described processes have used a finely divided anhydrous potassium hydroxide powder in organic solvents such as acetaldehyde-dibutyl acetal (U.S. Pat. No. 2 385 546, U.S. Pat. No. 2 385 548 and U.S. Pat. No. 2 455 058), methylal and dioxane (cf. W. Ziegenbein; Einfuehrung der Aethinyl- und Alkinyl-Gruppe in organische Verbindungen, Verlag Chemie (1963)), diisopropyl ether (US 2 163 720) or tetrahydrofuran (DE-AS 26 28 145 (=U.S. Pat. No. 4,117,249)). A drawback of this approach is that increase in the water content of the potassium hydroxide used results in an increased consumption of KOH. Furthermore these suspensions in the abovementioned solvents are usually so highly viscous that proper mixing is rendered very difficult, and this viscosity problem cannot be avoided or mitigated by using a relatively high excess of solvent because the solvents used to date have been rather expensive and their recovery for re-use involves expensive procedures, making this approach economically prohibitive.

The process described in DE-PSS 20 08 675 (=GB 1,329,815) and 20 47 446 (=GB 1,354,011) employs, as the base, potassium alcoholates of aliphatic alcohols, and readily accessible aliphatic, cycloaliphatic or aromatic hydrocarbons are used as the solvent. However, this approach has the salient disadvantage that a suspension of finely divided potassium alcoholate in the solvent must be produced in a preliminary reaction.

When relatively long-chain aliphatic methyl ketones are reacted with acetylene, as described e.g. in DE-PS 26 28 145 (=U.S. Pat. No. 4,117,249), only an incomplete conversion of the ketone is attained in tetrahydrofuran when technical potassium hydroxide is used as the base. These unsatisfactory results are obtained even when a ratio of KOH to ketone of 2:1 is used. Moreover, this process usually produces a mixture of the monoalcohol and the desired acetylene glycol of the general formula I.

There is thus a strongly felt need for a process which permits the manufacture of alkynediols by the reaction of ketones with acetylene, providing high yields economically and with a variety of different ketones.

SUMMARY OF THE INVENTION

Accordingly, it is an object of this invention to provide a novel process for the manufacture of alkynediols by reacting ketones with acetylene.

It is another object of this invention to provide an economical process for the manufacture of alkynediols from the reaction of ketones with acetylene.

It is another object of this invention to provide a novel process for the manufacture of alkynediols, in high yields, from the reaction of ketones with acetylene.

Briefly, these objects and other objects of the present invention as hereinafter will become more readily apparent can be obtained in a process for producing an alkynediol by reacting a ketone with acetylene in the presence of potassium hydroxide where an alkyl-tert-butyl ether solvent is used and the potassium hydroxide is used in a molar ratio relative to the amount of ketone used of 1.0:1.0 to 1.6:1.0. The solvent used is a $C_{1-4}$ alkyl-tertbutyl ether. The ketone which can be used is a $C_{3-12}$ ketone.

DETAILED DESCRIPTION OF THE PREFERRED EMBODIMENTS

It has now been surprisingly found that when using a $C_{1-4}$ alkyl-tert-butyl ether or a combination thereof, preferably methyl-tert-butyl ether (MTB) and/or ethyl-tert-butyl ether (ETB), in particular methyl-tert-butyl ether, as a solvent, the aforesaid disadvantages which have plagued the earlier processes described above are avoided.

Potassium hydroxide powder is used as the base. The potassium hydroxide used preferably has a water content of from 10 to 24% by weight, preferably 12 to 15% by weight. In this process the conversion of the carbonyl compounds with acetylene to form the corresponding alkynediols is advantageously carried out at temperatures ranging from 20° to 55° C., preferably 30° to 50° C. The carbonyl component and the acetylene are preferably introduced into a suspension composed of potassium hydroxide and $C_{1-4}$ alkyl-tert-butyl ether synchronously in a stoichiometric ratio corresponding to the desired reaction. Preferably the ketone and the acetylene are employed in a molar ratio of from 1:1 to 3:1, in particular a molar ratio of 1.8:1 to 2.2:1. The process of this invention provides reaction mixtures which can be stirred easily.

After the reaction is completed, water is added and the KOH is separated in the form of a caustic soda solution almost quantitatively by phase separation. The organic phase is neutralized with an organic acid, e.g. formic acid, acetic acid or a homologues thereof and the product is separated by distillation. The solvent thus recovered can be re-used without further purification. The whole operation is generally conducted at atmospheric pressure.

Suitable carbonyl compounds which can be used include aliphatic, araliphatic, aromatic and cyclic ketones containing from 3 to 12 carbon atoms. In particular acetone, methylethylketone, methylisobutylketone, methylisoamylketone and cyclohexanone can be used.

The process is carried out in that the components, potassium hydroxide and the ketone, are brought to reaction in a molar ratio of 1.0:1.0 to 1.6:1.0, preferably a molar ratio of 1.2:1.0 to 1.5:1.0.

The products produced according to this process are valuable intermediate products for the pharmaceutical and perfume industries. Other acetylene glycols are employed for the manufacture of surfactant preparations. Conversion with hydrogen peroxide results in hydroperoxides which are employed as polymerization initiators.

Other features of this invention will become apparent in the course of the following descriptions of exemplary embodiments which are given for illustration of this invention and are not intended to be limiting thereof.

EXAMPLES

Example 1

600 ml of methyl-tert-butyl ether and 478 g of potassium hydroxide powder (88%, the rest is $H_2O$) are suspended in a reactor fitted with a stirrer and at the same time 5 moles of methylisobutyl ketone (MIBK) and 60 liters acetylene are introduced. A constant temperature of 35° C. is maintained by cooling. After the conversion has been completed, hydrolysis takes place with 3,4 liters water and 458 g 2,4,7,9-tetramethyl-dec-5-yne-4,7-diol are isolated from the organic phase by vacuum distillation. This corresponds to a yield of 81% based on the amount of MIBK employed. The proportion of monoalcohol is low being only 5.5%.

Comparable results are attained if the ethyl-tertbutyl ether is employed instead of methyl-tert-butyl ether.

Example 2

The reaction described in Example 1 was carried out with 542 g potassium hydroxide powder (88%) and 5,7 moles of MIBK and 68 liters acetylene. 79% of the ketone introduced was isolated in the form of the acetylene glycol besides 7.5% of the monoalcohol.

Example 3

In a procedure analogous to that according to Example I MIBK In converted at a constant reaction temperature of 40° C., using water saturated MTB as a solvent to an extent of 78% to the acetylene glycol and to an extent of 3.4% to the monoalcohol.

Example 4

According to Example 1, at a constant reaction temperature of 40° C., 448 g 2,4,7,9-tetramethyl-dec-5-yne-4,7-diol are obtained from 6 moles of MIBK and 72 l acetylene. 9% of the ketone starting material is converted into the monoalcohol.

Example 5

In a procedure as described in Example 3 at a reaction temperature of 40° C., 229 g 2,5,8,11-tetramethyl-dodec-6-yne-5,8-diol-are formed from 3 moles of methylisoamyl ketone and 36 l acetylene in the presence of 287 g potassium hydroxide powder. The conversion to monoalcohol is minor, being only 5%.

Comparative example A 5 moles of MIBK and 60 l acetylene are converted at a temperature constantly maintained at 35° C. in a readily stirrable suspension of 600 ml anhydrous tetrahydrofuran and 478 g potassium hydroxide powder (88%). After hydrolysis and phase separation 400 g of the acetylene glycol (corresponding to 71% of the ketone employed) and 10% in the form of the monoalcohol are recovered by vacuum distillation.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by letters patent of the United States is:

1. In a process for manufacturing and recovering an alkynediol by reacting a ketone, acetylene and potassium hydroxide, the improvement comprising:
   synchronously reacting a $C_{3-12}$ ketone, acetylene, potassium hydroxide and $C_{1-4}$ alkyl-t-butyl ether solvent, wherein said potassium hydroxide is present as aqueous KOH having a water content of 10 to 24% by weight in a molar ratio relative to said ketone ranging from 1.0:1.0 to 1.6:1.0.

2. The process of claim 1, wherein said $C_{1-4}$ alkyl-t-butyl ether is methyl-t-butyl ether.

3. The process of claim 1, wherein the molar ratio of said potassium hydroxide to said ketone ranges from 1.2:1.0 to 1.5:1.0.

4. The process of claim 1, wherein said $C_{3-12}$ ketone is acetone, methyl ethyl ketone, methyl isobutyl ketone, methyl isoamyl ketone, or cyclohexanone.

5. The process of claim 1, wherein the molar ratio of said ketone to said acetylene ranges from 1.0:1.0 to 3.0:1.0.

6. The process of claim 1, wherein the molar ratio of said ketone to said acetylene ranges from 1.8:1.0 to 2.2:1.0.

7. The process of claim 1, wherein the water content of the potassium hydroxide powder ranges from 12 to 15% by weight.

8. The process of claim 1, wherein said reaction is conducted at a temperature ranging from 20°–55° C.

9. The process of claim 8, wherein said temperature ranges from 30°–50° C.

* * * * *